United States Patent [19]
Doleans et al.

[11] Patent Number: 5,691,195
[45] Date of Patent: Nov. 25, 1997

[54] APPLICATOR DEVICE FOR A FLAT ELEMENT FOR SAMPLING OF MICROORGANISMS, SUCH AS A PETRI DISH

[75] Inventors: Francis Doleans, Lyons; Alain Bonnet, Craponne; Sylvain Baeyaert, Saint-Genis-les-Ollieres, all of France

[73] Assignee: Bio Merieux, Marcy l'Etoile, France

[21] Appl. No.: 532,653

[22] PCT Filed: Mar. 10, 1995

[86] PCT No.: PCT/FR95/00285

§ 371 Date: Nov. 7, 1995

§ 102(e) Date: Nov. 7, 1995

[87] PCT Pub. No.: WO95/24463

PCT Pub. Date: Sep. 14, 1995

[30] Foreign Application Priority Data

Mar. 10, 1994 [FR] France .................. 94 03027

[51] Int. Cl.$^6$ .................. C12M 1/26; C12M 1/28
[52] U.S. Cl. .................. 435/309.1; 435/309.3; 435/809; 73/864.71
[58] Field of Search .................. 435/309.1, 309.4, 435/809; 73/864.71

[56] References Cited

U.S. PATENT DOCUMENTS

| | | | |
|---|---|---|---|
| 3,066,342 | 12/1962 | Jackson et al. | 73/864.71 |
| 3,074,276 | 1/1963 | Moos | 73/864.71 |
| 3,897,688 | 8/1975 | Meserol et al. | 435/309.4 |
| 4,103,553 | 8/1978 | De Blasiis et al. | 73/864.71 |
| 4,717,667 | 1/1988 | Provonchee | 435/309.4 |

FOREIGN PATENT DOCUMENTS

| | | | |
|---|---|---|---|
| 0150775 | 8/1985 | European Pat. Off. | |
| 58-111679 | 7/1983 | Japan | 435/309.1 |
| WO93/17090 | 9/1993 | WIPO | |

*Primary Examiner*—William H. Beisner
*Attorney, Agent, or Firm*—Oliff & Berridge

[57] ABSTRACT

An applicator device for a flat element (1) for sampling of microorganisms has a flat recess (3) for containing and retaining a culture medium (4), and with at least one border (5) arranged to the outside of the recess, wherein the applicator device has a plate (6), a base (7) for holding the plate at a distance from the surface (2) from which the sample is to be taken, defining a support surface (9), and forming an opening (7a) for engaging the sampling element (1) parallel with respect to the support surface (9), and with the free surface (4a) of the culture medium directed downwards, a pusher (10) mounted so as to be free in terms of translation on the plate (6) perpendicular to the support surface (9), with a bearing head (11) which protrudes from the inside of the base (7), a device (12) for returning the pusher towards the support surface (9) and at least one shoulder (13) defining a bearing surface (14) for retaining the border (5) of the sampling element (1).

11 Claims, 1 Drawing Sheet

APPLICATOR DEVICE FOR A FLAT ELEMENT FOR SAMPLING OF MICROORGANISMS, SUCH AS A PETRI DISH

BACKGROUND OF THE INVENTION

Hygiene control is a critical factor, especially in industrial and hospital environments. In this respect, various systems or devices have been developed for checking of air and of liquids. There may be mentioned, by way of example, the RCS germ collector, from the Biotest company, for determining the gem content of air, and the germ indicator, for determining the germ content in a liquid medium, marketed by this same company under the name Hycon.

Despite checking the quality of air and of liquids, there is still a major risk associated with the contamination of surfaces. In this respect, several companies have developed suitable culture media in dishes which ensure growth of the microorganisms taken directly from the contaminated surfaces and which permit a direct reading of the number of colonies in the dish. There may be mentioned, by Way of example, the Count-Tact medium or dish (reference 43501) marketed by the company BIO MERIEUX. The samples are taken, after the cover has been removed from the dish, by applying manual pressure to the bottom of the dish, for an unspecified period of time, in such a way that the agar medium comes into the closest possible contact with the surface from which the sample is to be taken.

Notwithstanding the optimization of the media in dishes for bacterial growth after taking samples from surfaces, the technique of manual application hitherto used suffers from various disadvantages.

One major disadvantage lies in a lack of reproducibility of the results—an important condition, particularly when monitoring the biocontamination of surfaces or checking sterility—principally due to variations in contact between the agar medium and the surface to be checked as a consequence of the differences in the manual force applied to the dish, which manual force can vary considerably from one operator to another, or even between different samples taken by one and the same operator.

This has therefore been the motivation for designing a device for applying media in dishes to surfaces which are to be checked, which device remedies the lack of reproducibility of the results by standardizing the pressure applied, irrespective of the surface to be tested and of its inclination, and which device furthermore permits control of the duration of application. Thus, the device according to the invention aims to standardize sampling from a surface by making it possible to obtain a predetermined bearing force for a controlled period of time.

SUMMARY OF THE INVENTION

In a general manner, the present invention relates to an applicator device for any flat element for sampling of microorganisms, comprising at least one flat recess for containing and retaining a layered culture medium, and with at least one border arranged to the outside, for example around the said recess, below the free surface of the culture medium in the flat recess. This general definition covers a large number of different embodiments of the flat sampling element, particularly the one described hereinbelow with reference to the drawings.

In order to cooperate with a sampling element, such as has been defined hereinabove, the applicator device according to the invention comprises:

—a plate,

—a base for holding the plate at a distance from the contaminated surface from which the sample is to be taken or which is to be tested, defining a support surface, and forming an opening for introducing, and placing under the plate, the sampling element, in its position of contact with the contaminated surface, that is to say upside down, parallel to the support surface, and with the free surface of the culture medium directed downwards, —a pusher mounted so as to be free in terms of translation on the plate, perpendicular with respect to the support surface, with a bearing head which protrudes inside the base, —a means for returning the pusher towards the support surface, —and at least one shoulder defining a bearing surface parallel to the support plane, for retaining the border of the sampling element, in its position of contact with the surface from which the sample is to be taken or which is to be tested, and to do this counter to the pusher.

By virtue of the invention, it suffices to place the sampling element in its position of contact with the surface from which the sample is to be taken, in the inner recess defined by the base, with the border of the said element being retained by the shoulder of the said base, in order to obtain an assembly which is ready to be applied by the user against and in contact with the surface to be tested. It suffices in fact to apply the free surface of the culture medium against the surface from which the sample is to be taken, and to press against the applicator device, which has the effect of pushing back or retracting the flat sampling element to the inside of the base, bringing at least the central part of the free surface of the culture medium in line or in contact with the surface to be tested, and to do this counter to the pusher, and more precisely counter to its return means. However, this being the case, the force of application or pressure against the flat sampling element is no longer that applied by the user, but instead that calibrated or predetermined in accordance with the return force exerted against the pusher.

BRIEF DESCRIPTION OF THE DRAWINGS

The present invention is now described with reference to the attached drawing, in which.

DESCRIPTION OF PREFERRED EMBODIMENTS

Figure 1:
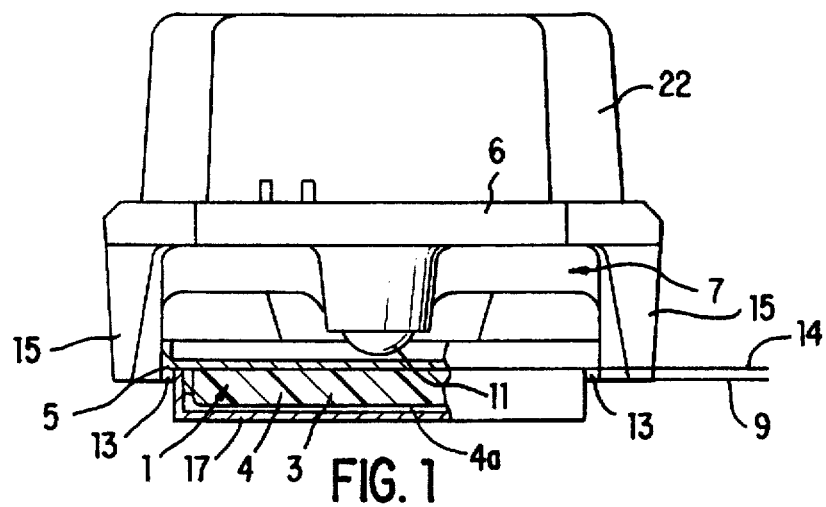
FIG. 1 represents a side view of an applicator device according to the invention, in which a flat element for sampling of microorganisms has been engaged.
Figure 2:
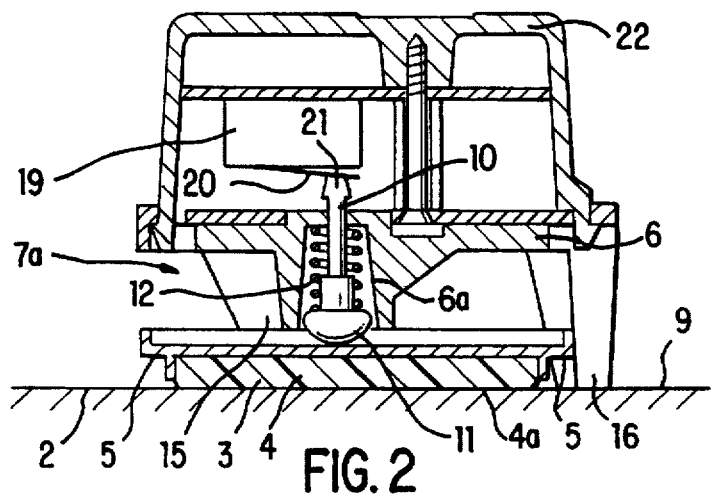
FIG. 2 represents a cross-section of the assembly represented in FIG. 1, in the sampling position against and in contact with the surface from which the sample is to be taken.

The device according to the invention is intended to cooperate with, and is adapted in shape and size to, a flat element 1 for sampling of microorganisms, particularly having the shape of a circular Petri dish made of transparent plastic. This flat element, obtained for example by an injection operation or thermoforming, comprises a flat recess 3 containing and retaining a relatively solid culture medium 4 distributed in a layer in the said recess, for example an agar medium. This same flat circular element comprises a circular border 5 arranged outside the recess 3 below the edge of the latter, and in particular the free surface 4a in the shape of a convex meniscus, of the culture medium 4. A removable circular cover 17 is associated with the flat circular sampling element 1 for the purpose of closing, by fitting thereon, the recess 3 for the culture medium 4.

In a general manner, the applicator device according to the invention, made of injection-moulded plastic for example, comprises:

— a plate 6 of general triangular shape,

— a base 7 for holding the plate at a distance from the contaminated surface from which the sample is to be taken, the said base defining a support surface 9, and forming an opening 7a for introducing and placing the sampling element 1 in a position of contact with the surface 2 from which the sample is to be taken, that is to say parallel with respect to the support surface 9, and with the surface 4a of the culture medium 4 directed downwards, — a pusher 10 mounted so as to be free in terms of translation on the plate 6 in a recess 6a of the latter, with a bearing head 11 which protrudes inside the base, and an opposite end 21 whose function will be made clear hereinafter, — a means or spring 12 for returning the pusher 10 towards the support surface 9, — two shoulders 13 situated inside the base 7 and defining a bearing surface 14 parallel with respect to the support plane 9, for retaining the border 5 of the sampling element 1, in its position of contact with the surface 2 from which the sample is to be taken, counter to the pusher 10.

Figure 3:
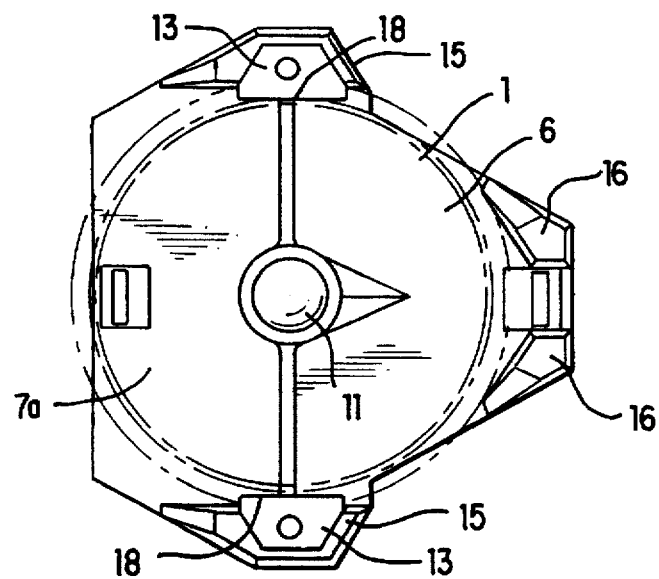
FIG. 3 represents a bottom view of the applicator device according to the invention, represented in FIGS. 1 and 2.

As is shown more particularly in FIG. 3, in which the position of contact of the sampling element 1 with the surface 2 from which the sample is to be taken is represented by dot-and-dash lines, the base 7 defines, in the plane of the bearing surface 14 of the shoulders 13, an internal polygon centred on the flat element 1, in its position of contact with the surface 2 from which the sample is to be taken.

The axis of the pusher 10 passes in a corresponding manner through the centre of this internal polygon.

Again as shown in FIG. 3, the base 7 comprises two feet 15 which are spaced apart, having a straight inner face and separated by a distance which, allowing for the functional clearance, is equal to the external diameter of the flat and circular sampling element 1, corresponding to the opening 7a of the base, as well as two feet 16 which are close to each other, opposite the opening 7a, ensuring the centring of the element 1.

Functionally, the course of free retraction of the flat sampling element 1 inside the base 7, counter to the return means 12 and perpendicular with respect to the support surface 9, corresponds to a distance greater than the height separating the free surface 4a of the flat element 1 from the support plane 9.

As is shown in FIG. 1, this makes it possible in particular to have a free surface 4a of the culture medium 4 protruding outside the base 7 before the element 1 is brought into contact with the surface 2 from which the sample is to be taken, which provokes the retraction of the element 1 inside the base 7.

The two shoulders 13 are associated with the two spaced-apart feet 15 and consist of two small plaques set flat against the lower face of the said feet 15. These same small plaques, forming shoulders, also constitute means 18 for holding or clamping the cover 17 in the position of contact of the sampling element 1 described above. Thus, the user can place the flat element 1 in the applicator device according to the invention, with its cover, remove it at the last moment, then replace it on the flat element once the sampling has been effected, and can do this prior to the withdrawal of the sampling element from the applicator device according to the invention.

Furthermore, the device according to the invention comprises, in a casing 22 which the user grips, a member 19 for controlling the application of the flat sampling element 1 on the surface 2 from which the sample is to be taken, which member 19 is attached in a removable manner, but can be made integral with the plate 6. This member 19 comprises means 20 for activation by the pusher 10, these means 20 being arranged in relation with the end 21 of the pusher 10, forming an abutment against the plate 6, opposite the head 11 bearing against the sampling element 1. The control member comprises, in a manner which is not represented, a timing means which in turn activates a device warning of the end of the application time, in the position of contact with the surface 2 from which the sample is to be taken, for example an acoustic warning device, or a visual warning device.

By virtue of this control member, the applicator device according to the invention makes it possible to standardize not only the force of application against the surface from which the sample is to be taken, but also the time of application against this surface.

We claim:

1. A portable hand-operated and passive applicator device, which is set on a surface (2) from which a sample is to be taken, said applicator device comprising:

a frame (6,7) comprising a base (7) defining a support surface (9) on said surface (2), and a side opening (7a) for introducing and extracting laterally a replaceable flat sampling element (1) in a reverse upright position for sampling a microorganism on the surface (2), and complementary retaining means (13) located inside said base, arranged for slidably engaging an external border (5) of said sampling element (1);

a pusher (10) slidably mounted on a plate (6) in said frame (6,7) in a direction perpendicular to said support surface (9), wherein said pusher comprises a bearing head (11) for slidably engaging the back of said sampling element when said sampling element is in its reverse position, in order to contact the sampling element with the surface (2); and biasing means (12) mounted between said pusher (10) and said frame, for returning said pusher towards the support surface (9), wherein said sampling element comprises a disk defining an internal recess (3) and the external border (5), and a layer of a culture medium (4) contained in said internal recess which defines a sampling surface (4a) above said border, when said sampling element is in a normal upright position for culturing the sampled microorganism.

2. Applicator Device according to claim 1, wherein the sampling element (1) is of circular shape, and wherein in the plane of a bearing surface (14) of the complementary retaining means (13), the base (7) defines an internal polygon centered on the sampling element (1) in its position of contact with the surface (2) from which the sample is to be taken.

3. Device according to claim 2, wherein the axis of the pusher (10) passes through the centre of the internal polygon.

4. Device according to claim 2, wherein the base (7) comprises two feet (15) which are spaced apart, having a straight inner face and separated by a distance which, allowing for the functional clearance, is equal to the external diameter of the sampling element (1), as well as two feet (16) which are close to each other, opposite the side opening (7a) of the base, ensuring the centering of the circular sampling element.

5. Device according to claim 1, wherein a course of free retraction of the sampling element (1) inside the base (7), counter to the return means (12), and perpendicular with respect to the support surface (9), corresponds to a distance greater than the height separating the sampling surface (4a) of the sampling element (1) from the support surface (9).

6. Device according to claim 1, adapted to match a sampling element (1) with a removable cover (17) closing the internal recess (3) for the culture medium, wherein the base (7) comprises means (18) for holding the cover (17) in a position of contact of the sampling element (1) with the surface (2) from which the sample is to be taken.

7. Device according to claim 6, characterized in that the means (18) for holding the cover are means for clamping the cover.

8. Device according to claim 1, wherein the device comprises a control member (19) for controlling the application of the sampling element (1) on the surface (2) from which the sample is to be taken, wherein the control member (19) is attached to or made integral with the plate (6), the control member (19) comprising means (20) for activation by the pusher (10) and being arranged in relation with the an end (21) of the pusher (10), opposite the bearing head (11).

9. Device according to claim 8, wherein the control member (19) comprises a timing means which in turn activates a device warning of an end of the application time.

10. Device according to claim 9, wherein the control member (19) is arranged in a removable manner with respect to the plate (6).

11. Device according to claim 9, wherein the warning device is an acoustic warning device.

* * * * *